(12) United States Patent
San Gabriel et al.

(10) Patent No.: US 7,157,250 B2
(45) Date of Patent: Jan. 2, 2007

(54) GLUTAMIC ACID RECEPTOR AND UTILIZATION THEREOF

(75) Inventors: Ana San Gabriel, Kawasaki (JP);
Takami Maekawa, Kawasaki (JP);
Hisayuki Uneyama, Kawasaki (JP);
Kunio Torii, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 71 days.

(21) Appl. No.: 10/828,332

(22) Filed: Apr. 21, 2004

(65) Prior Publication Data

US 2005/0003481 A1    Jan. 6, 2005

(51) Int. Cl.
C12P 21/06    (2006.01)
C07K 5/00    (2006.01)

(52) U.S. Cl. .................. 435/69.1; 530/324; 435/320.1; 435/325; 536/23.5

(58) Field of Classification Search ............... 435/69.1, 435/6
See application file for complete search history.

(56) References Cited

FOREIGN PATENT DOCUMENTS

WO    WO 97/05252    2/1997

OTHER PUBLICATIONS

Chaudhari, N., et al., "A metabotropic glutamate receptor variant functions as a taste receptor". Nature Neuroscience, Feb. 2000, vol. 3, No. 2, pp. 113-119.
Niijima, A., "Effects of oral and intestinal stimulation with umami substance on gastric vagus activity". Physiology & Behavior, 1991, vol. 49, No. 5, pp. 1025-1028.
Dingledine, R. & Conn, P. J., "Peripheral glutamate receptors: molecular biology and role in taste sensation". Journal of Nutrition, Apr. 2000, vol. 130, No. 4S, Suppl., pp. 1039S-1042S.
O'Hara, P. J., et al., "The ligand-binding domain in metabotropic glutamate receptors is related to bacterial periplasmic binding proteins". Neuron, 1993, vol. 11, pp. 41-52.
Han, G. & Hampson, D. R., "Ligand binding to the aminoterminal domain of the mGluR4 subtype of metabotropic glutamate receptor". J. Biol. Chem., 1999, vol. 274, No. 15, pp. 1008-1013.
Peltekova, V., et al., "Constraints on proper folding of the amino terminal domains of group iii metabotropic glutamate receptors". Molecular Brain Research, 2000, vol. 76, pp. 180-190.
Bernard, E. A., "Ionotropic glutamate receptors: new types and new concepts". TiPS, May 1997, vol. 18, pp. 141-148.
Schoepp, D. D., et al., "Metabotropic glutamate receptors in brain function and pathology". TiPS, Jan. 1993, vol. 14, pp. 13-20.
Tanabe, Y., et al., "A family of metabolic glutamate receptors". Neuron, Jan. 1992, vol. 8, pp. 169-179.
Flor, P. J., et al., "Molecular cloning, functional expression and pharmacological characterization of the human metabotropic glutamate receptor type 4". Neuropharmacology, 1995, vol. 34, No. 2, pp. 149-155.

Berk. M., et al., "Platelet Glutamate receptor supersensitivity in major depressive disorder". Clinical Neuropharmacology, 2001, vol. 24, No. 3, pp. 149-155.
Karim, F., et al., "Metabotropic glutamate receptor subtypes 1 and 5 are activators of extracellular signal-regulated kinase signaling required for inflammatory pain in mice". Journal of Neuroscience, Jun. 1, 2001, vol. 21, No. 11, pp. 3771-3779.
Berk, M., et al., "The specificity of platelet glutamate receptor supersensitivity in psychotic disorders". Life Sciences, 2000, vol. 66, No. 25, pp. 2427-2432.
Carlton, S. M., et al., "Inflammation-induced changes in peripheral glutamate receptor polulations". Brain Research, 1999, vol. 820, pp. 63-70.
Haxhiu, M. A., et al., "The role of excitatory amino acids in airway reflex responses in anesthetized dogs". Journal of the Autonomic Nervous System, 1997, vol. 67, pp. 192-199.
Inagaki, N., et al., "Expression and role of ionotropic glutamate receptors in pancreatic islet cells". The FASEB Journal, May 1995, vol. 9, pp. 686-691.
Erdö, S. L., "Excitatory amino acid receptors in the mammalian periphery". TiPS, Nov. 1991, vol. 12, pp. 426-429.
Aas, P., et al., "Stimulation of peripheral cholinergic nerves by glutamate indicates a new peripheral glutamate receptor". European Journal of Pharmacology, 1989, vol. 164, pp. 93-102.
Said, S., et al., "Glutamate signaling in the lung". TRENDS in Pharmacological Sciences, Jul. 2001, vol. 22, No. 7, pp. 344-345.
Skerry, T. M., et al., "Glutamate signaling in non-neuronal tissues". TRENDS in Pharmacological Sciences, Apr. 2001, vol. 22, No. 4, pp. 174-181.
Bray, G. A., "3$^{rd}$ plenary session on 'signaling in body-weight homeostasis' afferent signals regulating food intake". Proceedings of the Nutrition Society, 2000, vol. 59, pp. 373-384.
Bray, G. A., "Nutrient balance and obesity: an approach to control of food intake in humans". Medical Clinics of North America, Jan. 1989, vol. 73, No. 1, pp. 29-45.
Mei, N., "Recent studies on intestinal vagal afferent innervation. Functional implications". Journal of the Autonomic Nervous System, 1983, vol. 9, pp. 199-206.

(Continued)

*Primary Examiner*—Eileen O'Hara
*Assistant Examiner*—Gyan Chandra
(74) *Attorney, Agent, or Firm*—Nath & Associates PLLC; Gary M. Nath; Susanne M. Hopkins

(57) ABSTRACT

An agonist or antagonist of glutamic acid or an allosteric modulator is screened by reacting a glutamic acid receptor protein having the following properties with a substance binding thereto in the presence of a test substance and detecting the inhibition or promotion of the reaction:

(A) it has a transmembrane domain and an intracellular domain common to those of type 4 metabotropic glutamic acid receptor protein, or (B) it has an extracellular domain by about 316 or 327 amino acid residues shorter than that of the type 4 metabotropic glutamic acid receptor protein.

12 Claims, 3 Drawing Sheets

OTHER PUBLICATIONS

Mei, N., et al., "Current data and ideas on digestive sensitivity". Journal of the Autonomic Nervous System, 1992, vol. 41, pp. 15-18.

Mei, N., "Intestinal chemosensitivity". Physiological reviews, the American Physiological Society, Apr. 1985, vol. 65, No. 2 pp. 211-237.

Uezono, Y., et al., "Receptors that couple to 2 classes of G proteins increase cAMP and activate CFTR expressed in *Xenopus oocytes*". Receptors and Channels, vol. 1, pp. 233-241.

Cunningham, S. A., et al., "cAMP-stimulated ion currents in *Xenopus oocytes* expressing CFTR cRNA". American Physiological Society, 1992, pp. C783-C788.

Naples, M. A., et al., "Pharmacological profiles of the metabotropic glutamate receptor ligands [$^3$H]L-AP4 and [$^3$H]CPPG". Neuropharmacology, 2001, vol. 40, pp. 170-177.

Thomsen, C., et al., "Cloning and characterization of a metabotropic glutamate receptor, mGluR4b". Neuropharmacology, 1997, vol. 36, pp. 21-30.

Adams, S. R., et al., "Fluorescence ratio imaging of cyclic AMP in single cells". Nature, vol. 349, Feb. 21, 1991, pp. 694-697.

McConnell, H. M., et al., "The Cytosensor Microphysiometer: Biological applications of silicon technology". Science, vol. 257, Sep. 25, 1992, pp. 1906-1912.

Höfer, D. et al., "Taste receptor-like cells in the rat gut identified by expression of α- gustducin", *Proc. Natl. Acad. Sci. USA*, vol. 93 pp. 6631-6634, 1996.

Hampson, D.R. et al., "Probing the Ligand-Binding Domain of the mGluR4 Subtype of Metabotropic Glutamate Receptor", *The Journal of Biological Chemistry*, vol. 274(47) pp. 33488-33495, 1999.

Han, G. & Hampson, D.R., "Ligand Binding to the Amino-terminal Domain of the mGluR4 Subtype of Metabotropic Glutamate Receptor", Journal of Biological Chemistry, vol. 274, No. 15, pp. 10008-10013, (Apr. 9, 1999).

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:  primer

<400> SEQUENCE: 1
gaagttgacg ttcctgatgt act                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:  primer

<400> SEQUENCE: 2
acagcgtcaa tcacgaactg cac                                            23

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence:  primer

<400> SEQUENCE: 3
ctaatacgac tcactatagg gcaagcagtg gtaacaacgc agagt                    45

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:  primer

<400> SEQUENCE: 4
ctaatacgac tcactatagg gc                                             22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: primer
```

```
<400> SEQUENCE: 5
aagcagtggt aacaacgcag agt                                            23

<210> SEQ ID NO 6
<211> LENGTH: 1755
<212> TYPE: DNA
<213> ORGANISM: Rattus norvegicus
<220> FEATURE:
<221> NAME/KEY: CDS
<222> LOCATION: (1)..(1755)

<400> SEQUENCE: 6
```

| | | | | | | | | | | | | | | | | |
|---|---|---|---|---|---|---|---|---|---|---|---|---|---|---|---|---|
| atg | cca | ggg | gta | tca | tca | tct | ttg | cca | acg | agg | atg | aca | tca | ggg | ttc | 48 |
| Met | Pro | Gly | Val | Ser | Ser | Ser | Leu | Pro | Thr | Arg | Met | Thr | Ser | Gly | Phe | |
| 1 | | | | 5 | | | | | 10 | | | | | 15 | | |

| gac | cga | tac | ttc | tcc | agc | cgc | acg | ctg | gac | aac | aac | agg | cgc | aac | atc | 96 |
|---|---|---|---|---|---|---|---|---|---|---|---|---|---|---|---|---|
| Asp | Arg | Tyr | Phe | Ser | Ser | Arg | Thr | Leu | Asp | Asn | Asn | Arg | Arg | Asn | Ile | |
| | | | 20 | | | | | 25 | | | | | 30 | | | |

| tgg | ttt | gcc | gag | ttc | tgg | gag | gac | aac | ttc | cat | tgc | aag | ttg | agc | cgc | 144 |
|---|---|---|---|---|---|---|---|---|---|---|---|---|---|---|---|---|
| Trp | Phe | Ala | Glu | Phe | Trp | Glu | Asp | Asn | Phe | His | Cys | Lys | Leu | Ser | Arg | |
| | | 35 | | | | | 40 | | | | | 45 | | | | |

| cac | gcg | ctc | aag | aag | gga | agc | cac | atc | aag | aag | tgc | acc | aac | cga | gag | 192 |
|---|---|---|---|---|---|---|---|---|---|---|---|---|---|---|---|---|
| His | Ala | Leu | Lys | Lys | Gly | Ser | His | Ile | Lys | Lys | Cys | Thr | Asn | Arg | Glu | |
| 50 | | | | | 55 | | | | | 60 | | | | | | |

| cgc | atc | ggg | cag | gac | tcg | gcc | tat | gag | cag | gag | ggg | aag | gtg | cag | ttc | 240 |
|---|---|---|---|---|---|---|---|---|---|---|---|---|---|---|---|---|
| Arg | Ile | Gly | Gln | Asp | Ser | Ala | Tyr | Glu | Gln | Glu | Gly | Lys | Val | Gln | Phe | |
| 65 | | | | 70 | | | | | 75 | | | | | 80 | | |

| gtg | att | gac | gct | gtg | tac | gcc | atg | ggc | cac | gcg | ctg | cac | gcc | atg | cac | 288 |
|---|---|---|---|---|---|---|---|---|---|---|---|---|---|---|---|---|
| Val | Ile | Asp | Ala | Val | Tyr | Ala | Met | Gly | His | Ala | Leu | His | Ala | Met | His | |
| | | | 85 | | | | | 90 | | | | | 95 | | | |

| cgt | gac | ctg | tgt | ccc | ggc | cgc | gta | gga | ctc | tgc | cct | cgc | atg | gac | ccc | 336 |
|---|---|---|---|---|---|---|---|---|---|---|---|---|---|---|---|---|
| Arg | Asp | Leu | Cys | Pro | Gly | Arg | Val | Gly | Leu | Cys | Pro | Arg | Met | Asp | Pro | |
| | | 100 | | | | | 105 | | | | | 110 | | | | |

| gtg | gat | ggc | acc | cag | ctg | ctt | aag | tac | atc | agg | aac | gtc | aac | ttc | tca | 384 |
|---|---|---|---|---|---|---|---|---|---|---|---|---|---|---|---|---|
| Val | Asp | Gly | Thr | Gln | Leu | Leu | Lys | Tyr | Ile | Arg | Asn | Val | Asn | Phe | Ser | |
| | | 115 | | | | | 120 | | | | | 125 | | | | |

| ggc | att | gcg | ggg | aac | cct | gta | acc | ttc | aat | gag | aac | gga | gac | gca | ccg | 432 |
|---|---|---|---|---|---|---|---|---|---|---|---|---|---|---|---|---|
| Gly | Ile | Ala | Gly | Asn | Pro | Val | Thr | Phe | Asn | Glu | Asn | Gly | Asp | Ala | Pro | |
| 130 | | | | | 135 | | | | | 140 | | | | | | |

| ggg | cgc | tac | gac | atc | tac | cag | tac | caa | ctg | cgc | aat | ggc | tcg | gcc | gag | 480 |
|---|---|---|---|---|---|---|---|---|---|---|---|---|---|---|---|---|
| Gly | Arg | Tyr | Asp | Ile | Tyr | Gln | Tyr | Gln | Leu | Arg | Asn | Gly | Ser | Ala | Glu | |
| 145 | | | | 150 | | | | | 155 | | | | | 160 | | |

| tac | aag | gtc | atc | ggc | tcg | tgg | aca | gac | cac | ctg | cac | ctc | aga | ata | gag | 528 |
|---|---|---|---|---|---|---|---|---|---|---|---|---|---|---|---|---|
| Tyr | Lys | Val | Ile | Gly | Ser | Trp | Thr | Asp | His | Leu | His | Leu | Arg | Ile | Glu | |
| | | | 165 | | | | | 170 | | | | | 175 | | | |

| cgg | atg | cag | tgg | cca | ggg | agt | ggc | cag | cag | ctg | ccg | cgc | tcc | atc | tgc | 576 |
|---|---|---|---|---|---|---|---|---|---|---|---|---|---|---|---|---|
| Arg | Met | Gln | Trp | Pro | Gly | Ser | Gly | Gln | Gln | Leu | Pro | Arg | Ser | Ile | Cys | |
| | | | 180 | | | | | 185 | | | | | 190 | | | |

| agt | ctg | ccc | tgc | cag | ccc | ggg | gag | cga | aag | aag | act | gtg | aag | ggc | atg | 624 |
|---|---|---|---|---|---|---|---|---|---|---|---|---|---|---|---|---|
| Ser | Leu | Pro | Cys | Gln | Pro | Gly | Glu | Arg | Lys | Lys | Thr | Val | Lys | Gly | Met | |
| | | 195 | | | | | 200 | | | | | 205 | | | | |

| gct | tgc | tgc | tgg | cac | tgc | gag | ccc | tgc | acc | ggg | tac | cag | tac | caa | gtg | 672 |
|---|---|---|---|---|---|---|---|---|---|---|---|---|---|---|---|---|
| Ala | Cys | Cys | Trp | His | Cys | Glu | Pro | Cys | Thr | Gly | Tyr | Gln | Tyr | Gln | Val | |
| | 210 | | | | | 215 | | | | | 220 | | | | | |

| gac | cgc | tac | acc | tgt | aag | acc | tgc | ccc | tac | gac | atg | cgg | ccc | aca | gag | 720 |
|---|---|---|---|---|---|---|---|---|---|---|---|---|---|---|---|---|
| Asp | Arg | Tyr | Thr | Cys | Lys | Thr | Cys | Pro | Tyr | Asp | Met | Arg | Pro | Thr | Glu | |
| 225 | | | | 230 | | | | | 235 | | | | | 240 | | |

| aac | cgc | acg | agc | tgc | cag | ccc | atc | ccc | atc | gtc | aag | ttg | gag | tgg | gac | 768 |
|---|---|---|---|---|---|---|---|---|---|---|---|---|---|---|---|---|
| Asn | Arg | Thr | Ser | Cys | Gln | Pro | Ile | Pro | Ile | Val | Lys | Leu | Glu | Trp | Asp | |
| | | | 245 | | | | | 250 | | | | | 255 | | | |

```
tcg ccg tgg gcc gtg ctg ccc ctc ttc ctg gcc gtg gtg ggc atc gcc      816
Ser Pro Trp Ala Val Leu Pro Leu Phe Leu Ala Val Val Gly Ile Ala
        260                 265                 270 gcc acg ctg ttc gtg gtg gtc acg ttt gtg cgc tac aac gat acc ccc      864
Ala Thr Leu Phe Val Val Val Thr Phe Val Arg Tyr Asn Asp Thr Pro
            275                 280                 285 atc gtc aag gcc tcg ggc cgg gaa ctg agc tac gtg ctg ctg gcg ggc      912
Ile Val Lys Ala Ser Gly Arg Glu Leu Ser Tyr Val Leu Leu Ala Gly
290                 295                 300 atc ttt ctg tgc tac gcc act acc ttc ctc atg atc gca gag ccg gac      960
Ile Phe Leu Cys Tyr Ala Thr Thr Phe Leu Met Ile Ala Glu Pro Asp
305                 310                 315                 320 ctg ggg acc tgt tcg ctc cgc cgc atc ttc cta ggg ctc ggc atg agc     1008
Leu Gly Thr Cys Ser Leu Arg Arg Ile Phe Leu Gly Leu Gly Met Ser
                325                 330                 335 atc agc tac gcg gcc ctg ctg acc aag acc aac cgc att tac cgc atc     1056
Ile Ser Tyr Ala Ala Leu Leu Thr Lys Thr Asn Arg Ile Tyr Arg Ile
            340                 345                 350 ttt gag cag ggc aaa cgg tcg gtc agt gcc ccg cgt ttc atc agc ccg     1104
Phe Glu Gln Gly Lys Arg Ser Val Ser Ala Pro Arg Phe Ile Ser Pro
                355                 360                 365 gcc tcg cag ctg gcc atc acc ttc atc ctc atc tcc ctg cag ctg ctc     1152
Ala Ser Gln Leu Ala Ile Thr Phe Ile Leu Ile Ser Leu Gln Leu Leu
370                 375                 380 ggc atc tgc gtg tgg ttc gtg gtg gac ccc tcc cac tcg gtg gtg gac     1200
Gly Ile Cys Val Trp Phe Val Val Asp Pro Ser His Ser Val Val Asp
385                 390                 395                 400 ttc cag gac caa cgg aca ctt gac ccc cgc ttt gcc agg ggc gtg ctc     1248
Phe Gln Asp Gln Arg Thr Leu Asp Pro Arg Phe Ala Arg Gly Val Leu
                405                 410                 415 aag tgc gac atc tcg gac ctg tcc ctc atc tgc ctg ctg ggc tac agc     1296
Lys Cys Asp Ile Ser Asp Leu Ser Leu Ile Cys Leu Leu Gly Tyr Ser
                420                 425                 430 atg ctg ctg atg gtc acg tgt act gtg tac gcc atc aag acc cga ggc     1344
Met Leu Leu Met Val Thr Cys Thr Val Tyr Ala Ile Lys Thr Arg Gly
            435                 440                 445 gtg ccc gag acc ttc aac gag gcc aag ccc atc ggc ttc acc atg tac     1392
Val Pro Glu Thr Phe Asn Glu Ala Lys Pro Ile Gly Phe Thr Met Tyr
450                 455                 460 acc acc tgc att gtc tgg ctg gcc ttc atc ccc atc ttt ttt ggc acc     1440
Thr Thr Cys Ile Val Trp Leu Ala Phe Ile Pro Ile Phe Phe Gly Thr
465                 470                 475                 480 tca cag tca gcc gac aag ctg tac atc cag aca acc aca ctg acg gtc     1488
Ser Gln Ser Ala Asp Lys Leu Tyr Ile Gln Thr Thr Thr Leu Thr Val
                485                 490                 495 tcc gtg agt ctg agc gct tca gtg tcc ctg ggg atg ctc tac atg ccc     1536
Ser Val Ser Leu Ser Ala Ser Val Ser Leu Gly Met Leu Tyr Met Pro
            500                 505                 510 aaa gtc tac atc atc ctc ttc cac ccg gag cag aac gtg ccc aag cgc     1584
Lys Val Tyr Ile Ile Leu Phe His Pro Glu Gln Asn Val Pro Lys Arg
            515                 520                 525 aag cgc agt ctc aaa gcc gtg gtc acc gcc gcc acc atg tcc aac aag     1632
Lys Arg Ser Leu Lys Ala Val Val Thr Ala Ala Thr Met Ser Asn Lys
530                 535                 540 ttc aca cag aag ggc aac ttc agg ccc aat ggg gaa gcc aaa tca gag     1680
Phe Thr Gln Lys Gly Asn Phe Arg Pro Asn Gly Glu Ala Lys Ser Glu
545                 550                 555                 560 ctg tgt gag aac ctg gag acc cca gcg ctg gct acc aaa cag acc tac     1728
Leu Cys Glu Asn Leu Glu Thr Pro Ala Leu Ala Thr Lys Gln Thr Tyr
                565                 570                 575
```

```
gtc acc tac acc aac cat gcc atc tag                                    1755
Val Thr Tyr Thr Asn His Ala Ile
        580                 585

<210> SEQ ID NO 7
<211> LENGTH: 584
<212> TYPE: PRT
<213> ORGANISM: Rattus norvegicus

<400> SEQUENCE: 7

Met Pro Gly Val Ser Ser Leu Pro Thr Arg Met Thr Ser Gly Phe
 1               5                  10                  15

Asp Arg Tyr Phe Ser Ser Arg Thr Leu Asp Asn Asn Arg Arg Asn Ile
            20                  25                  30

Trp Phe Ala Glu Phe Trp Glu Asp Asn Phe His Cys Lys Leu Ser Arg
        35                  40                  45

His Ala Leu Lys Lys Gly Ser His Ile Lys Lys Cys Thr Asn Arg Glu
    50                  55                  60

Arg Ile Gly Gln Asp Ser Ala Tyr Glu Gln Glu Gly Lys Val Gln Phe
65                  70                  75                  80

Val Ile Asp Ala Val Tyr Ala Met Gly His Ala Leu His Ala Met His
                85                  90                  95

Arg Asp Leu Cys Pro Gly Arg Val Gly Leu Cys Pro Arg Met Asp Pro
            100                 105                 110

Val Asp Gly Thr Gln Leu Leu Lys Tyr Ile Arg Asn Val Asn Phe Ser
        115                 120                 125

Gly Ile Ala Gly Asn Pro Val Thr Phe Asn Glu Asn Gly Asp Ala Pro
    130                 135                 140

Gly Arg Tyr Asp Ile Tyr Gln Tyr Gln Leu Arg Asn Gly Ser Ala Glu
145                 150                 155                 160

Tyr Lys Val Ile Gly Ser Trp Thr Asp His Leu His Leu Arg Ile Glu
                165                 170                 175

Arg Met Gln Trp Pro Gly Ser Gly Gln Gln Leu Pro Arg Ser Ile Cys
            180                 185                 190

Ser Leu Pro Cys Gln Pro Gly Glu Arg Lys Lys Thr Val Lys Gly Met
        195                 200                 205

Ala Cys Cys Trp His Cys Glu Pro Cys Thr Gly Tyr Gln Tyr Gln Val
    210                 215                 220

Asp Arg Tyr Thr Cys Lys Thr Cys Pro Tyr Asp Met Arg Pro Thr Glu
225                 230                 235                 240

Asn Arg Thr Ser Cys Gln Pro Ile Pro Ile Val Lys Leu Glu Trp Asp
                245                 250                 255

Ser Pro Trp Ala Val Leu Pro Leu Phe Leu Ala Val Val Gly Ile Ala
            260                 265                 270

Ala Thr Leu Phe Val Val Thr Phe Val Arg Tyr Asn Asp Thr Pro
        275                 280                 285

Ile Val Lys Ala Ser Gly Arg Glu Leu Ser Tyr Val Leu Leu Ala Gly
    290                 295                 300

Ile Phe Leu Cys Tyr Ala Thr Thr Phe Leu Met Ile Ala Glu Pro Asp
305                 310                 315                 320

Leu Gly Thr Cys Ser Leu Arg Arg Ile Phe Leu Gly Leu Gly Met Ser
                325                 330                 335

Ile Ser Tyr Ala Ala Leu Leu Thr Lys Thr Asn Arg Ile Tyr Arg Ile
            340                 345                 350
```

```
                                   -continued

Phe Glu Gln Gly Lys Arg Ser Val Ser Ala Pro Arg Phe Ile Ser Pro
            355                 360                 365

Ala Ser Gln Leu Ala Ile Thr Phe Ile Leu Ile Ser Leu Gln Leu Leu
    370                 375                 380

Gly Ile Cys Val Trp Phe Val Val Asp Pro Ser His Ser Val Val Asp
385                 390                 395                 400

Phe Gln Asp Gln Arg Thr Leu Asp Pro Arg Phe Ala Arg Gly Val Leu
                405                 410                 415

Lys Cys Asp Ile Ser Asp Leu Ser Leu Ile Cys Leu Leu Gly Tyr Ser
                420                 425                 430

Met Leu Leu Met Val Thr Cys Thr Val Tyr Ala Ile Lys Thr Arg Gly
            435                 440                 445

Val Pro Glu Thr Phe Asn Glu Ala Lys Pro Ile Gly Phe Thr Met Tyr
    450                 455                 460

Thr Thr Cys Ile Val Trp Leu Ala Phe Ile Pro Ile Phe Phe Gly Thr
465                 470                 475                 480

Ser Gln Ser Ala Asp Lys Leu Tyr Ile Gln Thr Thr Thr Leu Thr Val
                485                 490                 495

Ser Val Ser Leu Ser Ala Ser Val Ser Leu Gly Met Leu Tyr Met Pro
                500                 505                 510

Lys Val Tyr Ile Ile Leu Phe His Pro Glu Gln Asn Val Pro Lys Arg
            515                 520                 525

Lys Arg Ser Leu Lys Ala Val Val Thr Ala Ala Thr Met Ser Asn Lys
    530                 535                 540

Phe Thr Gln Lys Gly Asn Phe Arg Pro Asn Gly Glu Ala Lys Ser Glu
545                 550                 555                 560

Leu Cys Glu Asn Leu Glu Thr Pro Ala Leu Ala Thr Lys Gln Thr Tyr
                565                 570                 575

Val Thr Tyr Thr Asn His Ala Ile
            580

<210> SEQ ID NO 8
<211> LENGTH: 14
<212> TYPE: PRT
<213> ORGANISM: Rattus norvegicus

<400> SEQUENCE: 8

Met Pro Gly Val Ser Ser Ser Leu Pro Thr Arg Met Thr Ser
1               5                   10
```

GLUTAMIC ACID RECEPTOR AND UTILIZATION THEREOF

RELATED APPLICATION

This application claims priority of International Patent Application PCT/JP02/10984 filed on Oct. 23, 2002, and of Japanese Patent Application No. 2001-325159 filed Oct. 23, 2001.

TECHNICAL FIELD

The present invention relates to novel glutamic acid receptor and utilization thereof, and more specifically to a glutamic acid receptor, DNA which encodes the receptor, a method of screening a ligand that binds to the receptor utilizing the same, a receptor binding test and so forth.

BACKGROUND ART

Glutamic acid is the major excitatory neurotransmitter in the central nervous system and it is widely accepted that anomaly of its control is involved in creation of pathological conditions of progressive encephalopathies such as disorder in memory, ischemic encephalopathy, amyotropic lateral sclerosis (ALS), Parkinson's disease, and Huntingon's chorea (Meldrum, B. S., Meruolgy, 1994 November;44 (11 Supple 8):S14–23; Nishizawa, Y., Life Sci. 2001, Jun. 15;69(4):369–81). This led to many studies on glutamic acid receptors throughout the cranial nerves, resulting in discovery of many types of receptors (three ionic type receptors and eight metabolic type receptors) in the central nervous system. With a view to developing therapeutic medicines for the above-mentioned diseases, even now development of agonists specific to such receptors is being energetically made (for details, reference is made to Barnard, E. A., Trends Pharmacol. Sci., 1997, May; 18(5):141–8; Schoepp, D. D., Conn, P. J., Trends Pharmacol. Sci. 1993 January; 14(1):13–20).

On the other hand, there are few studies on glutamic acid receptors other than in central nervous system. Glutamic acid is known to serve also as an energy source and a source for trapping ammonia that is no longer necessary and always exist in blood plasma in an amount on the order of several tens micromoles or more. In the central nervous system, the concentration of intracellular glutamic acid is on the order of nanomoles or less due to the existence of blood-brain barrier. As a result, the affinity of the above-mentioned glutamic acid receptor discovered in the central nervous system for glutamic acid is on the order of nanomoles to micromoles, so that the glutamic acid receptor can act only when glutamic acid is released from the nerve ending. In addition, the glutamic acid receptor tends to be inactivated or cause tachyphylaxis; in the central nervous system, gliacytes always take up glutamic acid through specific transporters to lower extracellular concentration of glutamic acid. On the other hand, in those sites other than the central nervous system where no protection by the blood-brain barrier is available, if glutamic acid receptors are expressed, it is considered that the glutamic acid receptors are always in a stimulated state and thus actually are inactivated and do not function.

However, in 2001, Chaudhari, N., Landin, A. M., Roper, S. D. et al. discovered low affinity glutamic acid receptor as an "umami" receptor from rat gustatory bud cells (Nat. Neurosci. 2000, February; 3(2):113–9). The umami receptor is gustatory type mGluR4, which has the same host gene as type 4 (mGluR4), a subtype of rat brain type metabotropic type glutamic acid receptor (Tanabe, Y. et al., Neuron, 1992, January;8)1):169–79; Flor, P. J. et al., Neuropharamacology, 1995, February;34(2):149–55) and is partially defective of extracellular domain of the brain type mGluR4 due to splicing mutation.

Today, we have several pieces of knowledge that suggest physiological functions of the peripheral glutamic acid receptor (Berk, M., Plein, H., Ferreira, D., Clin. Neuropharmacol., 2001, May-June;24(129–32; Karim, F., J. Neurosci. 2001, Jun. 1;21(11):3771–9; Berk, M., Plein, H., Belsham, B., Life Sci. 2000;66(25):2427–32; Carlton, S. M., Goggeshall, R. E., Brain Res. 1999, Feb. 27;820(1–2):63–70; Haxhij. M. A., Erokwu, B., Dreshaj, I. A., J. Auton. Nerv. Syst. 1997, Dec. 11;67(3):192–9; Inagaki, N., FASEB J. 1995, May;9(8):686–91; Erdo, S. L., Trends Pharamcol. Sci., 1991, November;12(11):426–9; Aas, P., Tanso, R., Fonnum, F., Eur. J. Pharamacol. 1989, May 2;164(1):93–102; Said, S. I., Dey, R. D., Dickman, K., Trends Pharmacol. Sci. 2001, July;22(7):344–5; Skerry, T. M., Genever, P. G., Trends Pharamacol., Sci. 2001, April; 22(4):174–81).

Incidentally, for mammals including humans to make normal growth and maintain normal (healthy) life, it is necessary to orally take up necessary amounts of nutrients at necessary timing and excrete unnecessary matter. This is actually done by a digestive tract, which is a single tube consisting of oral cavity, stomach, small intestine and large intestine. The process of digestion and absorption is controlled by intrinsic intestinal neuroplexus and extrinsic cranial nerves. The judgment at to whether or not to take a necessary nutrient is performed by integration in the brain of a pathway that the individual is aware of (taste) with an autonomous pathway that the individual is unaware of (visceral sense). It is considered that salty taste (sodium, potassium, etc.) serves as a marker of minerals and is useful for maintaining the osmotic pressure of the body fluid; the sweetness (glucose) serves as a marker of carbohydrates and is useful for supplementing energy; umami (sodium glutamate) serves as a marker of protein source and is useful for supplementing energy and body protein; and bitterness serves as a marker of toxic substances. That is, necessary nutrients are taken up relying on the tastes thereof. Then, if the necessary amounts are fully taken up is judged based on satiety that is obtained through a series of intracerebral processes of signal input to nucleus solitary tract from the afferent pathway of activated vagus nerve through nutrient sensors existing in the stomach, small intestine, and liver-portal vein (Bray, G. A., Proc. Nutr. Soc., 2000;59:373–84; Bray G. A., Med. Clin. North. Am. 1989:73:29). In addition, it is considered that digestion and absorption (secretion of digestive enzymes, enterokinesis, etc.) are controlled through efferent pathway of the vagus nerve. However, details of the mechanism are unclear. Then, finally satiety is obtained and eating behavior is terminated. In case of eating a substance toxic to the organism (poison), it is considered to be discharged by vomiting or diarrhea through humoral and neural responses. In this case too, details of the mechanism are unclear.

On the other hand, physiological studies on the mechanism of chemical sense in the digestive tract have been performed since a long time ago and it is supposed that there is a sensor that senses the content in the digestive tract (for the details, reference is made to Mei, N., J. Auton. Nerv. Syst., 1983;9:199–206; Mei, N., Lucchini, S., J. Auton, Nerv. Syst., 1992;41:15–8). The digestive sensors include a glucose sensor (Mei, N., J. Physiol. (Lond.) 1978, 282, 485-5–6), a temperature sensor (El Ouazzani, T., Mei, N., Exp. Brain Res. 1979;15;34:419–34), an osmotic pressure sensor (Mei, N., Garnier, L., J. Auton. Nerv. Syst., 1986; 16:159–70), a pH sensor, an amino acid sensor (Mei, N., Physiol. Rev., 1985;65:211–37), and a pressure sensor (Barber, W. D., Burks, T. F., Gastroenterol Clin. North. Am. 1987; 16:521–4).

In particular, the sensor that recognizes glutamic acid was suggested by Niijima et al. from neural excitation that occurred when glutamic acid was administered in the digestive tract by using the technique of electrically grasping the neural activity in the stomach branch and abdominal cavity branch of the vagus nerve that controls mainly the stomach and small intestine, assuming that there is a mechanism that recognizes glutamic acid in the vagus nerve ending (Niijima, A., Physiol. Behav., 1991;49:1025–8).

DISCLOSURE OF THE INVENTION

Although many studies have been made on the glutamic acid receptor and digestive tract sensors as described above, to date, the substance of the glutamic acid sensor is unclear and no progress has been made in the studies. Failure of isolation of a receptor mechanism containing a glutamic acid sensor (receptor, transporter, etc.) that is necessary for the recognition of nutrients on the mucous membrane of the digestive tract prevented progress of research in this field. The inventors of the present invention thought that elucidation of the substance of glutamic acid sensor in the digestive tract would enable development of drugs and the like directed to control of the nutrient recognition mechanism described below.

That is, the nutrient recognition mechanism also plays an important role on satiety or surfeit and improves poor physical condition due to edacity and imbalance of taken-up nutrients due to deviated food habit. It is considered that anomaly in the recognition of nutrients in the digestive tract naturally results in disturbance in the overall process of digestion and absorption, thus causing edacity, deviated food habit, inappetence, indigestion, diarrhea, constipation, etc. More medically, it is considered to be the factor for digestive ulcers (stomach ulcer, duodendum ulcer) due to psychogenetic hyperphagia, cibophobia, obesity, anomaly of acid secretion, anomaly of blood flow in digestive tract, anomaly of secretion of digestive enzymes, etc., stress ulcers, drug-caused (NSAIDs, etc.) acute ulcers, ischemic ulcer (ischemic colitis), diabetes due to anomaly of secretion of insulin or anomaly of secretion of digestive tract hormone, heavy stomach, nausea, constipation, diarrhea, hypersensitivity vowel syndrome, etc. due to anomaly of motility and so forth.

Further, in recent years, abrupt increase in the obesity rate is a social phenomenon, being a social issue. Many of those who are obese are said to have decreased basal metabolism and tend to eat too much. How to control the appetite of those obese is of a great social concern. Many try to be on an undue diet. However, in most cases, they are unsuccessful. Thus, improving the mechanism of recognizing nutrient in the digestive tract and obtaining satiety by meal normally is very important to those who are obese.

The present invention has been made from the above-mentioned viewpoint and it is an object of the present invention to elucidate the substance of the glutamic acid sensor in the digestive tract and provide a technology utilizing it.

The inventors of the present invention have studied the distribution of receptors in the digestive tract by an immunohistological technique using an antibody that recognizes intracellular domain of metabotropic glutamic acid receptor (type 4). As a result, they have found that in the mucous membrane layers of small intestine and large intestine, there are type 4 metabotropic glutamic acid receptor (GluR4)-positive cells. In the small intestine and large intestine, mucus-producing cell (goblet cell) was mGluR4-positive. Then, cDNA that is supposed to be a novel glutamic acid receptor was successfully cloned from the samples of the small intestine and large intestine. It is highly probable that the glutamic acid receptor is a glutamic acid sensor in the digestive tract and it is considered that the cDNA of the receptor, purified receptor and cell expressing the receptor are useful for screening agents for controlling the function of the glutamic acid sensor in the digestive tract.

The present invention has been accomplished based on the above-mentioned findings and the gist of the present invention is as follows.

(1) A glutamic acid receptor protein having the following properties:

(A) it has a transmembrane domain and an intracellular domain common to those of type 4 metabotropic glutamic acid receptor proteins; and (B) it has an extracellular domain by about 316 or 327 amino acid residues shorter than that of the type 4 metabotropic glutamic acid receptor protein.

(2) The glutamic acid receptor protein according to (1), wherein the protein is expressed in rat small intestine and large intestine.

(3) The glutamic acid receptor protein according to (1), wherein the protein comprises an amino acid sequence consisting of an amino acid sequence shown in SEQ ID NO: 7 or an amino acid sequence consisting of amino acids numbers 12 to 584 in the amino acid sequence shown in SEQ ID NO:7.

(4) The glutamic acid receptor protein according to (3), wherein the sequence includes substitution, deletion, insertion or addition of one or a plurality of amino acid residues, and the protein can generate a second messenger by binding glutamic acid thereto.

(5) A DNA which encodes a glutamic acid receptor protein according to any one of (1) to (4) and does not express type 4 metabotropic glutamic acid receptor protein.

(6) A cell harboring a DNA which encodes the glutamic acid receptor protein according to any one of (1) to (4) in an expressible form.

(7) A method of producing glutamic acid receptor protein, comprising the steps of cultivating a cell harboring a DNA which encodes the glutamic acid receptor protein according to any one of (1) to (4) in an expressible form in a medium to produce the glutamic acid receptor protein, and collecting the glutamic acid receptor protein from the cell.

(8) A method of screening an agonist, an antagonist, or an allosteric modulator of glutamic acid, comprising the steps of reacting the glutamic acid receptor protein according to any one of (1) to (4) with a substance that binds to the protein in the presence of a test substance and detecting inhibition or promotion of the reaction.

(9) A method of screening an agonist of glutamic acid, comprising the steps of reacting a glutamic acid receptor protein according to any one of (1) to (4) and a test substance, and detecting the reaction.

(10) The method according to (8), wherein the cell according to claim 6 or a membrane fraction prepared from the cell is used as the glutamic acid receptor protein.

(11) The method according to (10), in which the inhibition or promotion of the binding is detected by a second messenger generated by the glutamic acid receptor protein.
(12) The method according to (9), wherein the cell according to claim 6 or a membrane fraction prepared from the cell is used as the glutamic acid receptor protein.
(13) The method according to (12), in which the inhibition or promotion of the binding is detected by a second messenger generated by the glutamic acid receptor protein.
(14) An antibody that specifically binds to the glutamic acid receptor protein according to any one of (1) to (4).
(15) A method of producing a drug for modulating a second messenger generated by binding glutamic acid to a glutamic acid receptor, comprising the steps of:
reacting the glutamic acid receptor protein according to any one of (1) to (4) with a substance that binds to the protein in the presence of a test substance and detecting inhibition or promotion of the reaction to screen an agonist, an antagonist, or an allosteric modulator of glutamic acid; and
preparing a pharmaceutical composition containing the agonist, antagonist, or allosteric modulator of glutamic acid obtained in the reacting step as an active ingredient.
(16) A method of producing a drug for modulating a second messenger generated by binding glutamic acid to a glutamic acid receptor, comprising the steps of:
reacting the glutamic acid receptor protein according to any one of (1) to (4) with a test substance and detecting the reaction to screen an agonist of glutamic acid; and
preparing a pharmaceutical composition containing the agonist of glutamic acid obtained in the reacting step as an active ingredient.

Hereinafter, the present invention will be described in detail.

The glutamic acid receptor protein of the present invention typically has an amino acid sequence consisting of amino acids numbers 12 to 584 in the amino acid sequence described in SEQ ID NO: 7 in the Sequence Listing. The open reading frame of the nucleotide sequence of rat cDNA encoding the protein is shown in SEQ ID NO: 6. In the 5'-terminal region of this sequence, there were found two methionine codons (base numbers 1 to 3, and 34 to 36) each of which is possibly the start codon. Although it is highly possible that the methionine codon on the N-terminal side is the start codon, it is also possible that the second methionine codon is the start codon. In any event, ligation of a suitable promoter to upstream of the nucleotide sequence shown in SEQ ID NO: 6 and expression of the resultant in a suitable cell enables production of an active glutamic acid receptor.

Comparison of the amino acid sequence described in SEQ ID NO: 7 with the brain type metabotropic glutamic acid type 4 receptor (mGluR4) indicated that the c-terminal sides (amino acids numbers 15 to 584 in SEQ ID NO: 7) matched but the N-terminal side of the amino acid sequence described in SEQ ID NO: 7 was shorter by 300 amino acid residues or more than mGluR4. As described later, the glutamic acid receptor protein of the present invention was considered to be a splicing variant derived from the gene common with that of mGluR4. Hereinafter, the glutamic acid receptor protein of the present invention will also be referred to as mGluR4 variant in some cases.

FIG. 1 shows the structures of mGluR4 and mGluR4 variant. mGluR4 consists of an intracellular domain, 7 transmembrane domains and an extracellular domain. The mGluR4 variant also has an intracellular domain and 7 transmembrane domains that have the same sequences as those of mGluR4. On the other hand, the extracellular domain of the mGluR4 variant is shorter by 316 amino acid residues if the first methionine codon is a start codon, or by 327 amino acids if the second methionine codon is a start codon, than mGluR4.

That is, the mGluR4 variant of the present invention has common transmembrane domain and intracellular domain with those of the type 4 metabotropic glutamic acid receptor protein and an extracellular domain that is by about 316 or 327 amino acid residues shorter than the type 4 metabotropic glutamic acid receptor protein.

Comparison of the cDNA sequence encoding the above-mentioned mGluR4 variant with the mRNA sequence of mGluR4 (O'Hara, et al., Neuron, 11:41, 1993) suggested that these are derived from the common gene. That is, generation of mGluR4 variant is presumed to be a result of elimination of the second exon in the mGluR4 gene by alternative splicing to generate frame shift, which in turn causes a stop codon to appear in the first exon and causes a start codon downstream thereof.

The mGluR4 variant of the present invention may be derived from a rat. Alternatively, so long as it can generate a second messenger when glutamic acid is bound thereto, the mGluR4 variant may be derived from any animal including mammalian such as human, monkey, mouse, dog, cow, and rabbit, birds, and fin. In the case where the mGluR4 variant is used as a component of pharmaceutical composition, it is preferably derived from a mammalian.

The mGluR4 variant of the present invention may be a protein having the amino acid sequence of SEQ ID NO: 7 or the amino acid sequence consisting of amino acid numbers 12 to 584 in SEQ ID NO: 7, or a protein having the amino acid sequence of SEQ ID NO: 7 including substitution, deletion, insertion or addition of one or a plurality of amino acids at one or a plurality of sites so long as it has properties that it can generate a second messenger when glutamic acid is bonded thereto.

The "plurality" as used herein varies depending on the positions of amino acid residues in the three-dimensional structure of the protein and the types of the amino acids, however, the number may be such that the homology with the amino acid sequence shown by SEQ ID NO: 7 is 80% or more, preferably 90% or more. More particularly, the plurality is 2 to 115, preferably 2 to 58, more preferably 2 to 30.

The glutamic acid receptor of the present invention may be in a purified or isolated form; however, when the activity is required, it is preferably in a form that is expressed in a suitable cell and localized in the membrane of the cell or in a form contained in a membrane fraction prepared from a cell in which the mGluR4 variant was expressed. Thus, the glutamic acid receptor of the present invention also includes cells that express mGluR4 variant or a membrane fraction prepared from such cells.

The mGluR4 variant can be obtained, for example, by introducing DNA that encodes the mGluR4 variant into a suitable host cell to express the mGluR4 variant. The above-mentioned DNA includes gene that encodes the mGluR4 variant, isolated from the chromosome of a cell of a mammalian such as mouse. When chromosomal gene is used, it is preferable that cDNA is used since it is considered necessary to control a post-transcriptional process such as splicing so that mGluR4 variant can be generated.

The cDNA of mGluR4 variant can be cloned by amplifying the cDNA of mGluR4 variant using RNA prepared from the small intestine or large intestine of a mammal such as a rat as a template and oligonucleotides shown in, for example, SEQ ID NOS: 1 to 5 as primers. In addition, since the structure of mGluR4 variant, particularly unique structure on the N-terminal region has been made clear by the present invention, cloning and identification of the cDNA of mGluR4 variant can be performed easily based on the structures. The open reading frame nucleotide sequence of the thus obtained cDNA of mGluR4 variant is shown in SEQ ID NO: 6.

The DNA which encodes the mGluR4 variant includes in addition to the nucleotide sequence shown in SEQ ID NO: 6, DNA which hybridizes with DNA having this nucleotide sequence or a probe that can be prepared from the same nucleotide sequence under stringent conditions and that encodes the mGluR4 variant. The "stringent conditions" means conditions whereby specific hybrid is formed but nonspecific hybrids are not formed. It is difficult to clearly express the conditions by numeric values; examples thereof include those conditions whereby DNAs having high homology, for example, DNAs having 50% or more, preferably 75% or more homology hybridize with each other but DNAs having a lower homology than that will not hybridize with each other, or those conditions whereby DNAs hybridize with each other under ordinary washing conditions in southern hybridization, i.e., at 60° C. and a salt concentration corresponding to 1×SSC, 0.1% SDS, preferably 0.1× SSC, 0.1% SDS.

Cells to which DNA encoding the mGluR4 variant is introduced include preferably animal cells, insect cells or yeast when the activity of mGluR4 variant is necessary, with animal cells being particularly preferable. Examples of cells that are considered to enable transient expression of the function by introducing a recombinant vector containing DNA encoding the mGluR4 variant include *Xenopus laevis* oocyte, Chinese hamster ovary (CHO), baby hamster kidney (BHK) cell, human embryonic kidney (HEK) cell, Sf-9 insect cell, PC12 cell, and COCA-2 cell. In addition, when DNA encoding the mGluR4 variant is incorporated in chromosomal DNA to express the mGluR4 variant permanently, those cells other than the *Xenopus laevis* oocyte are suitable.

On the other hand, when no physiological activity is necessary such as the case where the mGluR4 variant is used as an immunogen for preparing antibody that specifically binds to the mGluR4 variant, cells to which DNA encoding the mGluR4 variant is introduced may be those cells that do not express the mGluR4 variant in an active form. As such cells, microbial cells that are usually used for the production of heterologous protein, including *Escherichia coli* may be used.

To produce the mGluR4 variant in the host cell, DNA, which encodes the mGluR4 variant, is ligated to an expression regulation sequence such as promoter or enhancer suitable for the host cell. The DNA which encodes the mGluR4 variant may include a processing information site, for example, a ribosome binding site, an RNA splicing site, a polyadenylation site, and a transcription terminator sequence as necessary. Preferable expression control sequences include promoters derived from immunoglobulin gene, SV40, adenovirus, bovine papilloma virus, and cytomegalovirus.

The techniques necessary for the manipulation of cells such as introduction of DNA therein are described in, for example, Sambrook, J., Fritsch, E. F., and Maniatis, T., "Molecular Cloning A Laboratory Manual, Second Edition", Cold Spring Harbor Laboratory Press, (1989).

The mGluR4 variant and a cell that retains the mGluR4 variant can be produced by cultivating a cell that harbors the DNA encoding the mGluR4 variant obtained as described above in an expressible form in a medium to produce the mGluR4 variant.

Active mGluR4 variant, that is, mGluR4 variant that can generate a second messenger when glutamic acid is bound thereto can be utilized for screening agonist, antagonist or allosteric modulator of glutamic acid. For example, the mGluR4 variant and a substance that binds to the mGluR4 variant are reacted in the presence of a test substance, and inhibition or promotion of the reaction is detected, thereby screening agonist, antagonist or allosteric modulator of glutamic acid (hereinafter, these may be referred to collectively as "ligand"). The allosteric modulator binds to a site other than the binding site between the mGluR4 variant and glutamic acid to exhibit similar function to that of the agonist or antagonist.

Further, the agonist of glutamic acid may be screened by reacting the mGluR4 variant with a test substance and detecting the reaction.

The active mGluR4 variant may include cells that express the mGluR4 variant or membrane fractions prepared from such cells. Such membrane fractions may be prepared by allowing cells to express active mGluR4 variant, ultrasonically disrupting the cells, and subjecting the sonicate to density gradient centrifugation to collect a membrane fraction.

Further, examples of the substance that binds to the above-mentioned mGluR4 variant include glutamic acid, glutamic acid agonist, or known ligands that bind to mGluR4 (L-AP4, CPPG, MAP-4, or the like). The substances that modulate the activity of the mGluR4 variant include drugs that influence the intracellular concentration of calcium (calcium channel and sodium channel opener, Na/K pump inhibitor, Na/Ca exchange agonist, Ca-ATPase inhibitor, protein kinase C agonist), drugs that influence intracellular cAMP concentration (phosphodiesterase agonist, adenylate cyclase agonist), and drugs that influence intracellular cGMP concentration (cGMP-dependent phosphodiesterase agonist, guanylate cyclase agonist) and so forth.

Inhibition or promotion of the reaction between mGluR4 variant and a substance that binds thereto can be detected by measuring a second messenger that is generated by binding of a ligand such as glutamic acid to the mGluR4 variant. Alternatively, the above-mentioned inhibition or promotion of reaction can also be detected by measuring the binding of a labeled known ligand to the mGluR4 variant instead of detecting the second messenger.

Further, the reaction between the mGluR4 variant and the agonist of glutamic acid can be detected by detecting a second messenger that is generated by binding of the mGluR4 variant to the agonist of glutamic acid.

The intracellular domain of mGluR4 variant is the same as the brain type and gustatory bud type mGluR4 and the brain type and gustatory bud type mGluR4 have the same intracellular signal transmitting mechanism. Therefore, the mGluR4 variant is expected to have similar intracellular signal transmitting mechanism. Therefore, the above-mentioned second messenger is inhibition of production of intracellular cAMP accompanying activation of Gi (inhibitory GTP binding protein) to adenylate cyclase. Furthermore, downstream of cAMP in signal transmission includes regulation of gene expression through modulation of cAMP-responsive element and modulation of function of acute phase by phosphorylation of cytoplasm or membrane protein. Therefore, the second messenger can be detected by measuring change in the amount of cAMP accumulated in the cell, measuring change in intracellular calcium concentration through modulation of intracellular Ca-ATPase activity, or measuring change in the function of channel.

Hereinafter, examples of concrete method for screening ligands by using the mGluR4 variant will be explained below.

(1) The mGluR4 variant cRNA and CFTR (cystic fibrosis transmembrane conductance regulator) cRNA are allowed to coexpress in *Xenopus laevis* oocytes and screening of ligands that act on the mGluR4 variant is performed by a two electrode voltage clamp method by using increase or decrease in chloride current attributable to CFTR as an index (Uezono et al., Receptors Channels 1993;1(3): 233–41; Cunningham S A et al., Am. J. Physiol 1992 March;262(3 Pt 1):C783–8). CFTR is a causative gene product for cystic lung fibrosis and is a chloride channel whose activity is modulated by intracellular cAMP.

(2) The mGluR4 variant expressing cells and a candidate compound for ligand are allowed to coexist for a certain period of time, and then the amount of intracellular cAMP in the expressing cell is determined and screening of ligands is performed based on increase or decrease in the cAMP level (Chaudhari N, Nat Neurosci 2000 February; 3(2):113–9; Flor P J, Neuropharmacology 1995 February; 34(2)149–55). The amount of cAMP can be measured by using commercially available kits.

(3) Screening of ligands is performed by reacting a candidate compound for ligand and a known ligand that acts on mGluR4 (for example, glutamic acid, L-AP4, CPPG, MAP-4 or the like) on an mGluR4 variant expressing cell or a membrane fraction prepared from the cells for a certain period of time and measuring the amount of the known ligand bound to the cell membrane or membrane fraction of the mGluR4 variant expressing cells (Naples M A, Neuropharmacology 2001;40(2):170–7; Thomsen C, Neuropharmacology 1997 January;36(1)21–30; H. I. Yamamura, S. J. Enna and M. J. Kuhar eds, 1958, Neurotransmitter Receptor Binding, 2nd ed., Raven Press, New York). The amount of the known ligand can be measured by labeling a portion of the substances with radioactivity and determining the quantity of radioactivity bound to the cell membrane or membrane fraction.

(4) A calcium-sensitive dye (for example, Fura-2, Indo-1, Fluo-3 or the like) is introduced into an mGluR4 variant expressing cell in advance, and a ligand candidate compound and the mGluR4 variant expressing cells are allowed to contact for a certain period of time, and then ligands are screened by using as an index a change in a ratio of intensities of fluorescence (intracellular calcium concentration). Alternatively, screening of ligand is performed by a change in a ratio of intensities of fluorescence (intercellular calcium concentration) obtained when an mGluR4 variant agonist, a candidate compound for ligand, and an mGluR4 variant expressing cells into which a calcium-sensitive dye is introduced are allowed to contact for a certain period of time.

(5) Screening of ligands is performed by using as an index a change in a ratio of intensities of fluorescence (intracellular cAMP concentration) obtained when a cAMP-sensitive fluoroprotein (for example, FICRhR or the like) is introduced into an mGluR4 variant expressing cell in advance and then a ligand candidate compound and the mGluR4 variant expressing cells are allowed to contact for a certain period of time (Adams S R, Nature 1991 Feb. 21;349(6311):694–7).

(6) Screening of ligands is performed by using as an index the production amount of proton obtained when a candidate compound for ligand and an mGluR4 variant expressing cells are allowed to contact for a certain period of time, or when an mGluR4 variant agonist, a candidate compound for ligand and an mGluR4 variant expressing cells are allowed to contact for a certain period of time and measured by a cytosensor (McConnell H M, Science 1992 Sep. 25;257(5078):1906–12).

A pharmaceutical composition that comprises the agonist, antagonist or allosteric modulator of glutamic acid as an active ingredient thus screened can be used as a drug for modulating the second messenger generated when glutamic acid is bound to a glutamic acid receptor. Modulation of the second messenger enables improvement and prevention of diseases and pathology caused by anomaly of glutamic acid receptor.

The anomalies of control of vagus nerve include anomaly of afferent pathway (disorder of nutrient recognition) and anomaly of efferent pathway. The diseases or pathology due to the anomaly of afferent pathway include hyperphagia, cibophobia, obesity and so on. On the other hand, those due to the anomaly of efferent pathway include digestive ulcers (stomach ulcer, duodenum ulcer) due to psychogenetic hyperphagia, cibophobia, obesity, anomaly of acid secretion, anomaly of blood flow in digestive tract, anomaly of secretion of digestive enzymes, etc., stress ulcers, drug-caused (NSAIDs, etc.) acute ulcers, ischemic ulcer (ischemic colitis), diabetes due to anomaly of secretion of insulin or anomaly of secretion of digestive tract hormone, heavy stomach, nausea, constipation, diarrhea, hypersensitivity vowel syndrome, etc. due to anomaly of motility and so forth.

Use of mGluR4 variant as an immunogen enables preparation of an antibody that specifically binds to the mGluR4 variant. In particular, since the mGluR4 variant has a novel amino acid sequence in the N-terminus, antibody, particularly monoclonal antibody, that contains this portion as an epitope is expected to bind to the mGluR4 variant and not to bind to other glutamic acid receptors. The antibody specific to the mGluR4 variant can be used in immunostaining specific to the mGluR4 variant.

BEST MODE FOR CARRYING OUT THE INVENTION

Figure 1:
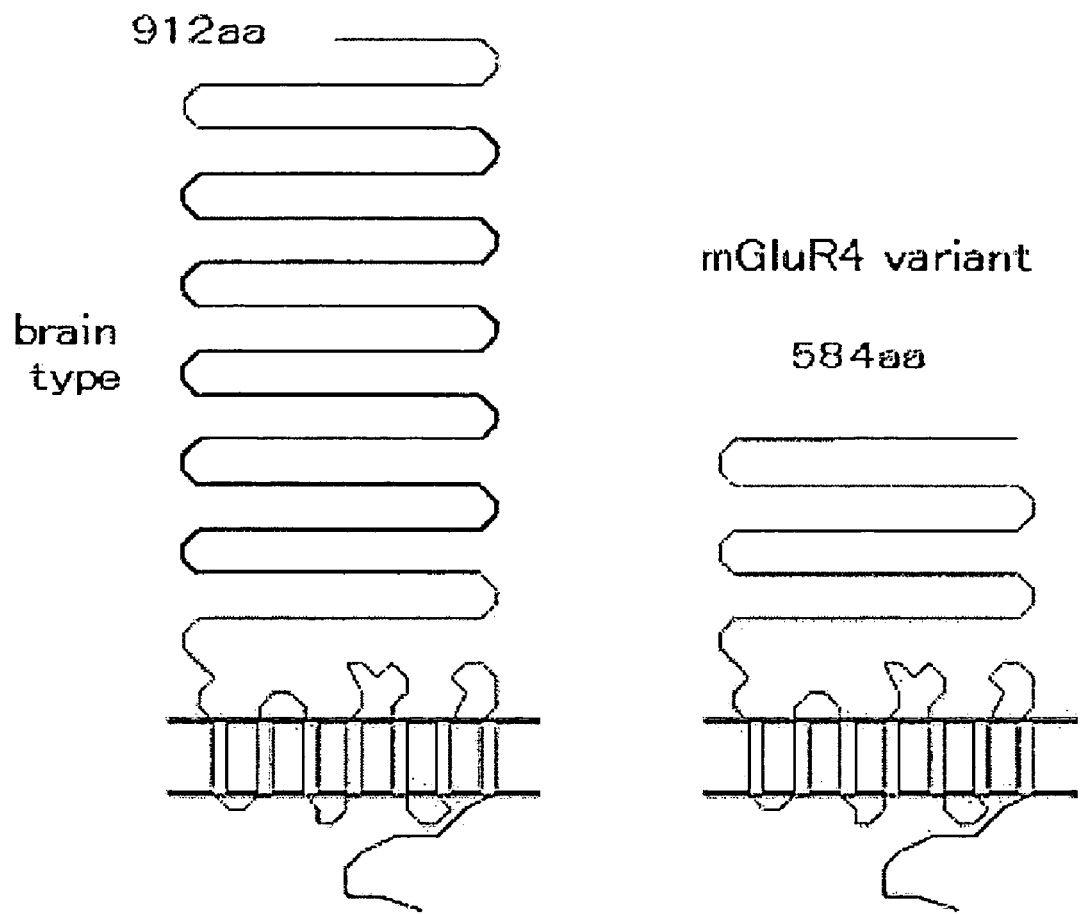
FIG. 1 is a schematic diagram showing the structures of mGluR4 and mGluR4 variant.

Hereinafter, the present invention will be described in detail through examples.

EXAMPLE 1

Cloning of Novel Metabotropic Glutamic Acid Receptor cDNA From Rat Intestinal Tissue Reverse transcription was performed by using superscript (Gibco-BRL) and SMART (Switching Mechanism at 5' end of RNA Transcript) RACE (rapid amplification of cDNA ends) cDNA amplification kit (Clontech) and using total RNA derived from small intestine and large intestine of a Wistar rat (CRJ) as a template. By using the obtained cDNA as a template, the 5' end fragment of rat mGluR4 was amplified by 5'-RACE using LA taq (TaKaRa) followed by nested PCR.

Gene specific primers (R-mGluR4: 5'-GAA GTT GAC GTT CCT GAT GTA CT-3' (SEQ ID NO: 1), R2-mGluR4: 5'-ACA GCG TCA ATC ACG AAC TGC AC-3' (SEQ ID NO: 2)) were synthesized based on the brain type mRNA sequence (O'Hara, et al., Neuron, 11:41, 1993).

The primers from SMART-RACE kit (Universal primer mix: Long 5'-CTA ATA CGA CTC ACT ATA GGG CAA GCA GTG GTA ACA ACG CAG AGT-3' (SEQ ID NO: 3), Short 5'-CTA ATA CGA CTC ACT ATA GGG C-3' (SEQ ID NO: 4), and Nested universal primer: 5'-AAG CAG TGG TAA CAA CGC AGA GT-3' (SEQ ID NO: 5)) were used for performing 5'-RACE PCR.

About 30 ng rat cDNA was amplified in 10 µl 10×LA PCR buffer, 2.5 mM $MgCl_2$, 2.5 mM dNTP mixure and 0.25 units La Taq enzyme by using gene-specific primer, R-mGluR4 and Universal primer mix.

PCR was performed 40 cycles by using a GeneAmp PCR system 9700 at 94° C. for 20 seconds, 50° C. for 1 minute, and 68° C. for 3 minutes, followed by chain extension at 68° C. for 10 minutes.

The obtained reaction product was amplified again by using R2-mGluR4 and Nested universal primer under the same conditions as described above to obtain a 300 bp fragment.

The amplification product was separated by electrophoresis on agarose and cloned in pCR-II vector having dual promoter by using TA cloning kit (Invitrogen).

Analysis of the nucleotide sequence of the above-mentioned fragment by using ABI Sequencer Model 3700 (ABI) identified clones named 010411-70, 010411-66, and 010528-3 from the large intestine and 010528-37 from the small intestine. They contained the same nucleotide sequence.

The nucleotide sequence identified from each of the above-mentioned clones is shown in SEQ ID NO: 6. In addition, the amino acid sequence encoded by the open reading frame contained in the nucleotide sequence is shown in SEQ ID NO: 7. Comparison of the nucleotide sequence with the mRNA sequence of brain mGluR4 (O'Hara, et al., Neuron, 11:41, 1993) revealed that in the nucleotide sequence of SEQ ID NO: 6, cytosine at position 1724 is directly liked to adenine at position 1880 (the positions of nucleotides are based on mGluR4 mRNA) and that 155 bp fragment is deleted. This suggests that the frame shift in the domain upstream of cytosine at position 1724 results in translation of a novel peptide (SEQ ID NO: 8) having methionine at the N-terminus that is encoded by a start codon starting at 1684 or 1717 and that the peptide linkes to glycine at position 343 located in the extracellular domain of the glutamic acid receptor. The remaining sequence was the same as the sequence of brain type receptor. A codon that starts at position 1684 is shown as the start codon in SEQ ID NO: 6 and SEQ ID NO: 7. Although it is unclear which of the two methionine codons the start codon is, it is expected in any event that introduction of the open reading frame and its peripheral sequence and expression thereof in a cell can give rise to the same expression product as that expressed in living organism.

The above-mentioned protein encoded by the open reading frame has a molecular weight of about 88 kD assuming that the first methionine in the amino acid sequence shown in SEQ ID NO: 7 is the N-terminus. Fourteen amino acids on the N-terminus does not exist in the amino acid sequence encoded by mGluR4 mRNA.

From the above, it is demonstrated that the obtained clone is a splicing variant of mGluR4 having a novel extracellular domain.

EXAMPLE 2

Identification of Localization of Glutamic Acid Receptor by Immunostaining

<1> Preparation of Sliced Samples of Rat Small Intestine and Large Intestine

Rats (Wistar strain, male, 10 to 15-week age) were let bleed by dissecting right auricle of the heart under anesthesia with ether and immediately thereafter, small intestine and large intestine were extracted. From the small intestine, a part about 5 cm from the outlet of stomach was extracted. From the large intestine, about 7 cm long part from the ileocecal opening on the side of rectum was extracted. When a large amount of digestion product remained in the intestine, the intestinal tract was washed with physiological saline.

The dissected intestinal tract was cut open, put on a cork board with a needle, and immersed in 4% paraformaldehyde (4° C.) with shaking for one day to fix it. Thereafter, the intestinal tract was immersed in 20% Sucrose-PBS for 3 to 4 days for cryprotection, wrapped in Tissue-Tek$^R$ (OCT compound), and then sliced to a thickness of 5 to 7 µm in a cryostat. The sections were dried at room temperature and then stored at 4° C. until use for various kinds of staining.

<2> Immunostaining Wit Anti-Metabotropic Glutamic Acid Receptor Antibody

Immunostaining of the sections was performed according to the method described in Drengk, A. C. et al., J. Auto. Nerv. Sys. 78: 109–112, 2000, and Miampamba, M. et al., J. Auto. Nerv. Sys. 77: 140–151, 1999. The sections were first washed with PBS and then treated with 3% hydrogen peroxide/methanol for 15 minutes in order to inhibit a reaction by endogenous peroxidase. Then, the sections were washed with PBS and blocked with 1% bovine serum albumin added PBS (1% BSA-PBS) containing 10% normal equine serum for 1 hour. After washing with PBS again, the sections were reacted with a primary antibody diluted with 1% BSA-PBS containing 1% normal equine serum (Table 1) at 4° C. for two overnights. Thereafter, the sections were washed with PBS and reacted with secondary antibody diluted with 1% BSA-PBS (Table 1) at room temperature for 1 hour. Finally, ABC (Avidin-Biotin Complex) reaction was performed using a Vectorstain elite kit (Vector), followed by color development with 0.025% diaminobenzidine-0.25% nickel chloride-0.01% $H_2O_2$. After completion of the reaction, the sections were washed with PBS, dehydrated with ethanol/xylene, and sealed and then observed under a microscope. A sample without primary antibody was used as a negative control. The kinds and dilution magnifications of primary antibody and of secondary antibody are shown in Table 1.

TABLE 1

| Primary antibody | Magnifications of primary antibody | Secondary antibody | Magnifications of primary antibody |
|---|---|---|---|
| anti-mGluR1a, rabbit, polyclonal, Chemicon, cat# AB1551 | 100 | Biotinylated anti-rabbit Ig, Amersham Pharmacia Biotech, cat# RPN 1004 | 150 |

TABLE 1-continued

| Primary antibody | Magnifications of primary antibody | Secondary antibody | Magnifications of primary antibody |
|---|---|---|---|
| anti-mGluR2/3, rabbit, polyclonal. Chemicon, cat# AB1553 | 100 | Biotinylated anti-rabbit Ig, Amersham Pharmacia Biotech, cat# RPN 1004 | 150 |
| anti-mGluR4a, rabbit, Upstate Biotechnology, cat# 06-765 | 400 | Biotinylatyed anti-rabbit Ig, Amercham Pharmacia Biotech, cat# RPN 1004 | 150 |
| anti-mGluR5, rabbit, polyclonal, Chemicon, cat# AB5323 | 400 | Biotinylated anti-rabbit Ig, Amersham Pharmacia Biotech, cat# RPN 1004 | 150 |

<3> Alcian Blue/PAS Stain

The sections were washed with running water, treated with 3% acetic acid, and then reacted with Alcian Blue solution (pH 2.5, WAKO) for 30 to 40 minutes. Then, the sections were washed with running water and immersed in 1% periodic acid solution for 10 minutes, followed by reaction with Schiff's reagent (WAKO) for 8 to 10 minutes. By the above treatment, mucin was stained to identify goblet cell of the intestinal tract. After washing the sections with running water again, finally, the sections were subjected to nuclear stain with Mayer's hematoxylin (WAKO), and after thus performing color intensification, the sections were dehydrated and sealed.

<4> Results

Figure 2:
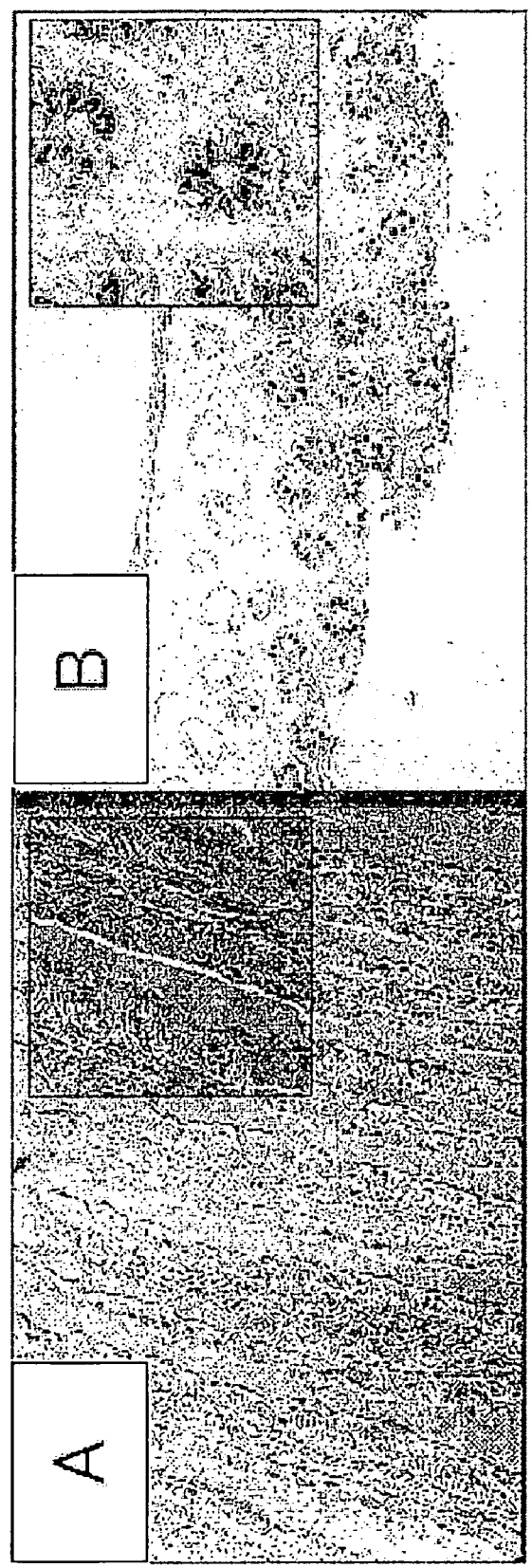
FIG. 2 is a photograph showing results of immunostaining with an anti-mGluR4 antibody. (A): small intestine. (B): large intestine.

The results of immunostaining are shown in FIG. 2. Regarding the small intestine (FIG. 2A) and large intestine (FIG. 2B), the goblet cells were stained with the anti-mGluR4. It is a general assumption that mGluR4 receptors are not expressed in the goblet cells. Therefore, it is conceived that the mGluR4 variant is expressed in the goblet cells, which suggests that the mGluR4 variant is functionally related to secretion of mucoid.

EXAMPLE 3

Presumption of the Function of Novel mGluR4 Variant

After starved for 18 hours, rats (Wistar strain, male, 8 to 10 week age: Japan Charles River) were laparotomized under anesthesis with urethane (1 g/kg, i.p.) and about 5 mm of the abdominal cavity branch of vagus nerve was peeled off under stereoscopic microscope. After the cutting of vagus nerve fasciculus, the vagus nerve fasciculus was placed on a small operation stage (8×6 mm) and fat and connective tissue surrounding the vagus nerve fasciculus were carefully peeled off. The terminal fiber on the organ side was placed on a platinum-made bipolar electrode and insulated from the surrounding tissue with liquid paraffin/vaseline (1:1) mixed solution. As an administration route of MSG (sodium L-glutamate, manufactured by Ajinomoto Corporation), a silicone tube was placed in the stomach and the origin part of duodendum orally.

The neural activity potential was amplified 10,000 folds by a micro potential amplifier (DAM-80 manufactured by WPI) and subjected to A/D conversion (Powerlab 4sp, manufactured by ADI Instruments) after noise was decreased by a Bessel filter (4-pole, High Cut 10 Hz, Low Cut 1 KHz). Thereafter, the potential was incorporated in a computer (sampling rate 3 KHz, iBook). Simultaneously, while monitoring the amplified signals by an oscilloscope, a noise component is separated from a neural signal component by a window discriminator (DSE-435, manufactured by DiaMedical Corporation), integrated for 5 seconds by a Spike Counter (DSE-335P, manufactured by Nihon Kohden Corporation) and recorded by a chart recorder (WT-465G, manufactured by Nihon Kohden Corporation). The waveform of spikes was analyzed by using SHE software (manufactured by ADI Instruments).

Figure 3:
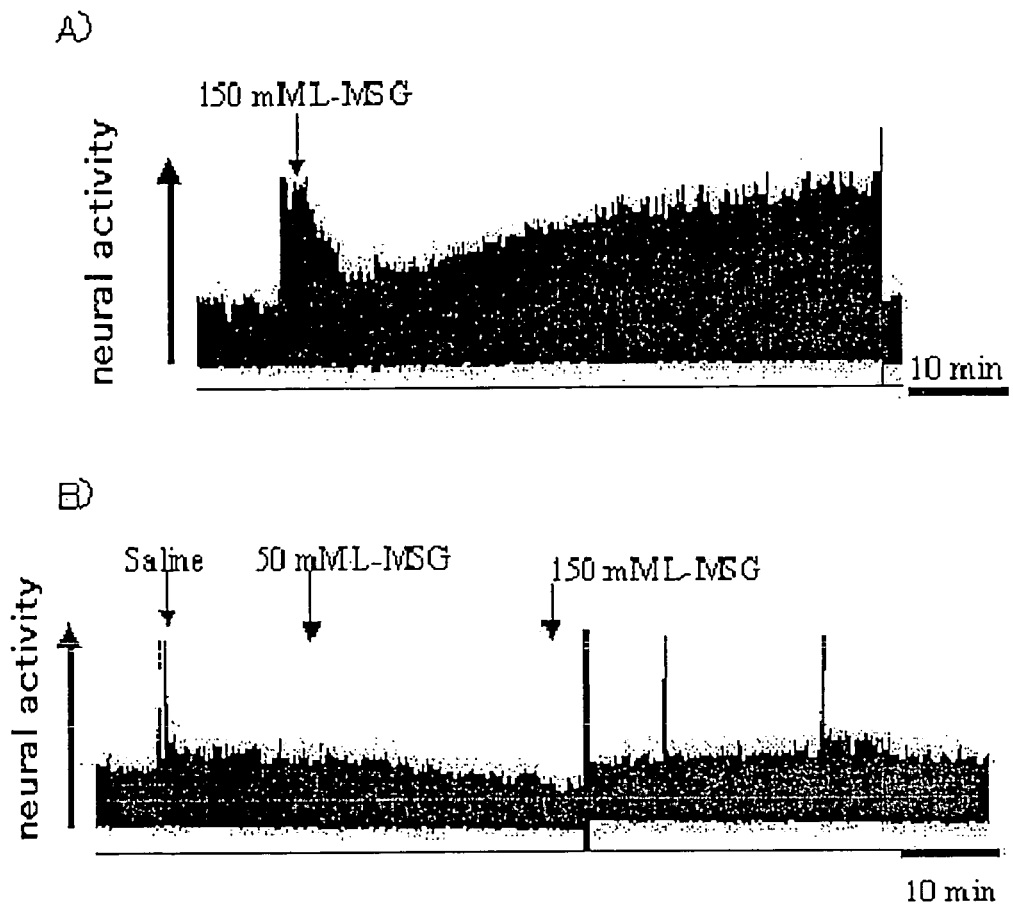
FIG. 3 is a diagram showing action of L-glutamic acid on afferent action of the abdominal branch of vagus nerve, with horizontal axis indicating time and vertical axis showing neuronal action.

The results obtained are shown in FIG. 3. The afferent activity of the abdominal cavity branch of vagus nerve when 150 mM MSD was administered in the duodendum was increased. The afferent pathway of vagus nerve is considered to be a signal transmitting pathway that transmits visceral sense, particularly nutrient information from the stomach and intestines to the nucleus solitary tract and performs control of postcibal sense such as satiety or sense of displeasure and digestion by modulating the efferent pathway of the vagus nerve. Therefore, increase in the activity of the afferent pathway of vagus nerve by the administration of MSG in the digestive tract indicates the possibility that MSG is a causative factor that generates the signal and the mGluR4 variant expressed in the lumen of the digestive tract mediates the generation of the signal.

EXAMPLE 4

Preparation of Novel mGluR4 Variant Expressing Cell

<1> Preparation of Novel mGluR4 Variant Expressing Cell

A full-length cDNA of a novel mGluR4 variant was amplified again by a RT-PCR method by using PFU polymerase (Promega). Then, the resultant was cloned in pUni-V5-His-TOPO by using a cloning kit (Invitrogen) according to a conventional method and thereafter, the cDNA was incorporated into pcDNA3.1E by using a plasmid fusing method.

The prepared vector (pcDNA3.1E) was introduced in CHO-K1 cell (Dainippon Pharmaceutical Co., Ltd.) by using polyFect reagent (Qiagen). After 48 hours, neomycin (600 μg/ml) was added to a culture medium (Modified Eagle Medium (αMEM) containing 10% fetal bovine serum, 100 U/ml penicillin; Nacalai Tesque) and cultivation was continued for 2 to 3 weeks to perform screening of gene-introduced cells. The screened CHO-K1 cell was proliferated to a cell number that is necessary for the evaluation of function after expression of mRNA of novel mGluR1 variant was confirmed by an RT-PCR method.

<2> Measurement of Function of mGluR4 Variant Gene by cAMP Measurement

The variant expressing cells obtained as described above were dispensed to $2.5 \times 10^5$ cells/well on a plate (24-well) and cultivated for 20 hours and then used for the measurement of the function of cAMP. Each plate was washed well with Dulbeco's phosphate buffer and incubated for 20 minutes. Thereafter, stimulation was performed with each drug for 10 minutes at 37° C. After the stimulation, the cells were at once treated with ice-cooled 2.5% perchloric acid (PCA) for 30 minutes, neutralized with KOH, and centrifuged to obtain a supernatant (12,000 rpm×10 min, 4° C.). The cAMP content of the supernatant was determined according to a conventional enzyme immunoassay (ELISA) by using a cAMP assay kit (Amersham).

As a result, the amount of cAMP in the mGluR4 variant expressing cell was increased about 9 folds by treatment with a phosphodiesterase inhibitor (isobutyl-methyl-xanthine; IBMX; 100 μM) and an adenyl cyclase activator (forskolin; 10 μM). Comparison of the actions of glutamic acid (1 mM) and sodium chloride (1 mM) under the above conditions revealed that the amount of cAMP was 1,519 fmole in the sodium chloride added group (n=3) and 1,235 fmole in the glutamic acid added group (n=3). This made it clear that the amount of cAMP accumulated in the mGluR4 variant expressing cell was decreased by about 19% by the addition of glutamic acid. This experimental results demonstrated that the novel mGluR4 variant reacts with glutamic acid on the order of millimoles and modulates the signal transduction system.

INDUSTRIAL APPLICABILITY

According to the present invention, a novel metabotropic glutamic acid receptor can be provided. The glutamic acid receptor can be used in screening agonists, antagonists or allosteric modulators of glutamic acid. In addition, the glutamic acid receptor can be used as a medicine for improving diseases and pathology due to metabolic disorder in digestive tracts such as small intestine and large intestine.

What is claimed is:

1. An isolated DNA molecule that encodes a glutamic acid receptor protein, comprising:
   receptor protein, wherein the protein comprises an amino acid sequence comprising SEQ ID NO: 7 or the amino acid sequence comprising amino acid residues 12 to 584 of SEQ ID NO: 7,
   wherein the glutamic acid receptor protein comprises
      a transmembrane domain and an intracellular domain common to those of brain type 4 metabotropic glutamic acid receptor protein, and
      an extracellular domain that is about 316 or 327 amino acid residues shorter than the extracellular domain of the brain type 4 metabotropic glutamic acid receptor protein.

2. The DNA molecule of claim 1, wherein the glutamic acid receptor protein is expressed in rat small intestine and large intestine.

3. An isolated cell comprising a DNA molecule that encodes the glutamic acid receptor protein of claim 2 in an expressible form.

4. A method of producing glutamic acid receptor protein, comprising:

cultivating a cell transformed with a DNA molecule encoding the glutamic acid receptor protein of claim 2 in an expressible form, in a medium to produce the glutamic acid receptor protein.

5. An isolated cell comprising a DNA molecule that encodes the glutamic acid receptor protein of claim 1 in an expressible form.

6. A method of producing glutamic acid receptor protein, comprising:

cultivating a cell transformed with a DNA molecule encoding the glutamic acid receptor protein of claim 1 in an expressible form, in a medium to produce the glutamic acid receptor protein.

7. An isolated DNA molecule that encodes a glutamic acid receptor protein and is hybridizable with a DNA molecule having a nucleotide sequence comprising SEQ ID NO: 6 under washing conditions of 60° C., 1×SSC, and 0.1% SDS, wherein the glutamic acid receptor protein comprises a transmembrane domain and an intracellular domain common to those of brain type 4 metabotropic glutamic acid receptor protein, and an extracellular domain that is about 316 or 327 amino acid residues shorter than the extracellular domain of the brain type 4 metabotropic glutamic acid receptor protein.

8. The DNA molecule of claim 7, wherein the glutamic acid receptor protein is expressed in rat small intestine and large intestine.

9. An isolated cell comprising a DNA molecule that encodes the glutamic acid receptor protein of claim 8 in an expressible form.

10. A method of producing glutamic acid receptor protein, comprising:

cultivating a cell transformed with a DNA molecule encoding the glutamic acid receptor protein of claim 8 in an expressible form, in a medium to produce the glutamic acid receptor protein.

11. An isolated cell comprising a DNA molecule that encodes the glutamic acid receptor protein of claim 7 in an expressible form.

12. A method of producing glutamic acid receptor protein, comprising:

cultivating a cell transformed with a DNA molecule encoding the glutamic acid receptor protein of claim 7 in an expressible form, in a medium to produce the glutamic acid receptor protein.

* * * * *

UNITED STATES PATENT AND TRADEMARK OFFICE
CERTIFICATE OF CORRECTION

PATENT NO. : 7,157,250 B2
APPLICATION NO. : 10/828332
DATED : January 2, 2007
INVENTOR(S) : San Gabriel et al.

It is certified that error appears in the above-identified patent and that said Letters Patent is hereby corrected as shown below:

Claim 1, Column 23, Lines 58-59,
Please delete "comprising: receptor protein,"

Claim 1, Column 23, Line 60,
Please delete "the" and replace with --an--

Claim 7, Column 25, Line 17,
Please delete "60° C.," and replace with --60° C,--

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

PATENT NO.         : 7,157,250 B2                                        Page 1 of 1
APPLICATION NO. : 10/828332
DATED              : January 2, 2007
INVENTOR(S)        : San Gabriel et al.

It is certified that error appears in the above-identified patent and that said Letters Patent is hereby corrected as shown below:

On The Title Page, Please insert:

Item (63)  Continuation of application No. PCT/JP02/10984
           filed on October 23, 2002

Item (30)  Foreign Application Priority Data
           October 23, 2001 (JP) 2001-325159

Signed and Sealed this

Twelfth Day of June, 2007

JON W. DUDAS
*Director of the United States Patent and Trademark Office*